United States Patent
Pedersen et al.

(10) Patent No.: US 11,911,222 B2
(45) Date of Patent: *Feb. 27, 2024

(54) MODEL-BASED CONTROL OF A DYNAMIC RANGE OF AN ULTRASOUND IMAGE

(71) Applicant: B-K Medical Aps, Herlev (DK)

(72) Inventors: Jens Mose Pedersen, Lyngby (DK); Svetoslav Ivanov Nikolov, Farum (DK)

(73) Assignee: BK MEDICAL APS, Herlev (DK)

( * ) Notice: Subject to any disclaimer, the term of this patent is extended or adjusted under 35 U.S.C. 154(b) by 14 days.

This patent is subject to a terminal disclaimer.

(21) Appl. No.: 17/304,864

(22) Filed: Jun. 28, 2021

(65) Prior Publication Data

US 2021/0321990 A1    Oct. 21, 2021

Related U.S. Application Data

(63) Continuation of application No. 15/966,405, filed on Apr. 30, 2018, now Pat. No. 11,076,835.

(51) Int. Cl.
*A61B 8/08*    (2006.01)
*G06T 5/00*    (2006.01)
*A61B 8/14*    (2006.01)
*A61B 8/00*    (2006.01)

(52) U.S. Cl.
CPC ............ *A61B 8/5269* (2013.01); *A61B 8/145* (2013.01); *A61B 8/5207* (2013.01); *A61B 8/54* (2013.01); *A61B 8/58* (2013.01); *G06T 5/002* (2013.01); *G06T 5/009* (2013.01); *G06T 2207/10132* (2013.01); *G06T 2207/20208* (2013.01)

(58) Field of Classification Search
None
See application file for complete search history.

(56) References Cited

U.S. PATENT DOCUMENTS

| | | | |
|---|---|---|---|
| 5,709,209 A * | 1/1998 | Friemel | A61B 8/06 600/447 |
| 5,993,392 A | 11/1999 | Roundhill et al. | |
| 6,120,446 A * | 9/2000 | Ji | G01N 29/2456 600/443 |
| 6,390,983 B1 * | 5/2002 | Mo | G01S 15/8981 600/453 |
| 6,704,437 B1 | 3/2004 | He et al. | |

(Continued)

*Primary Examiner* — Katherine L Fernandez
(74) *Attorney, Agent, or Firm* — Daugherty & Del Zoppo, Co. LPA

(57) ABSTRACT

A system includes a transducer array configured to produce a signal indicative of a received echo wave, receive circuitry configured to amplify and digitize the signal, sub-systems configured to process the digitized signal to generate an image including electronic noise from the system, and a system controller. The system controller is configured to retrieve a pre-determined noise level of an analog front end of the receive circuitry, configure the sub-systems, wherein each of sub-systems includes multiple processing blocks, and the configuring determines which of the processing blocks are employed and which of the processing blocks are bypassed for a scan, and determine a noise level for each of the employed sub-systems based on a corresponding noise model. The sub-systems include a processor configured to adaptively vary at least one of a gain and a dynamic range of the image as a function of depth based on the noise levels.

18 Claims, 8 Drawing Sheets

(56) References Cited

U.S. PATENT DOCUMENTS

2008/0015441 A1* 1/2008 Kanda ................. G01S 7/52033
600/459
2015/0126869 A1 5/2015 Kawabata
2019/0328368 A1 10/2019 Pedersen et al.

* cited by examiner

MODEL-BASED CONTROL OF A DYNAMIC RANGE OF AN ULTRASOUND IMAGE

TECHNICAL FIELD

The following generally relates to ultrasound imaging and more particularly to model-based of a dynamic range of an ultrasound image, which, in one instance, compensates the ultrasound image for electrical noise of hardware of the imaging system present in an echo signal used to generate the ultrasound image.

BACKGROUND

An ultrasound imaging system includes at least a transducer array with one or more transducing elements. For scanning a patient, the transducer array is positioned against the subject, and one or more of the transducing elements are excited to transmit a pressure wave which traverses the subject. An echo wave is produced in response to the pressure wave interacting with matter such as tissue, blood, etc. in the subject. The one or more transducing elements receive the echo wave and produce an electrical signal. Receive circuitry of the imaging system processes the electrical signal, and the processed electrical signal is indicative of both the received echo wave and electrical noise of an analog front-end of the receive circuitry.

The transmitted and echo waves are attenuated as they traverse the subject. As such, prior to processing the electrical signal, time gain compensation (TGC) is applied to amplify the electrical signal so that a signal for deeper tissue has approximately a same amplitude as a signal for more superficial tissue. The amplified signal includes an amplified echo signal and an amplified electrical noise signal, which increases with depth. Depending on the depth, the echo wave may be attenuated such that its amplitude is on an order of the noise, and the amplified noise will appear as a greyish background onto which the amplified ultrasound image appears.

As the greyish background image impacts contrast, a user may prefer to see the ultrasound image without the noise. To achieve this, the user manipulates the TGC curve based on depth so that the background noise is less visible at the cost of lowering echo signal brightness. FIG. 1 shows an example image in which the front-end gain of the system amplifies the echo signal and the noise at larger depths to a degree that the noise manifests in a greyish background 102. FIG. 2 shows the image after the noise is reduced through the TGC curve to remove much of the greyish background 102. Another approach is described in U.S. Pat. No. 5,993,392, which uses variable compression of variable dynamic range with depth and lateral scan dimensions.

Unfortunately, the above approaches require the system provide at least a sufficient analog gain for difficult cases and/or the user manually adjust the TGC whenever the echo strength, the electrical noise strength and/or the processing gain changes. Examples of such situations include, e.g. a depth change, a beamforming change, a change in compound parameters, harmonics on/off, pulsed wave Doppler being enabled, a change to a mode that needs lower transmit voltage in order not to exceed predetermined (e.g., FDA) limits or burst contrast bubbles, etc. To avoid user adjustment of the TGC curve, a maximum gain is pre-specified as a preset. Unfortunately, a maximum gain defines a hard limitation in penetration and creates an unnatural boundary in the displayed ultrasound image. Furthermore, it is time-consuming trying to define a correct maximum value and it depends on a sensitivity of the transducer used to create the preset.

SUMMARY

Aspects of the Application Address the Above Matters, and Others

In one aspect, an ultrasound imaging system includes a transducer array configured to produce a signal indicative of a received echo wave, receive circuitry configured to amplify and digitize the signal, processing sub-systems configured to process the digitized signal to generate an image including electronic noise from the system, and a system controller. The system controller is configured to retrieve a pre-determined noise level of an analog front end of the receive circuitry, configure the processing sub-systems, wherein each of processing sub-systems includes multiple processing blocks, and the configuring determines which of the processing blocks are employed and which of the processing blocks are bypassed for a scan, and determine a noise level for each of the employed processing sub-systems based on a corresponding noise model. The processing sub-systems includes a processor configured to adaptively vary at least one of a gain and a dynamic range of the image as a function of depth based on the noise levels.

In another aspect, a method includes retrieving a pre-determined noise level of an analog front end of receive circuitry of an ultrasound imaging system, configuring processing sub-systems of the ultrasound imaging system, wherein each of processing sub-systems includes multiple processing blocks, and the configuring determines which of the processing blocks are employed and which of the processing blocks are bypassed for a scan, determining a noise level for each of the employed processing sub-systems based on a corresponding noise model, and adaptively varying at least one of a gain and a dynamic range of an ultrasound image as a function of depth based on the noise levels.

In another aspect, a computer readable medium is encoded with non-transitory computer executable instructions which when executed by a processor causes the processor to: retrieve a pre-determined noise level of an analog front end of receive circuitry of an ultrasound imaging system, configure processing sub-systems of the ultrasound imaging system, wherein each of processing sub-systems includes multiple processing blocks, and the configuring determines which of the processing blocks are employed and which of the processing blocks are bypassed for a scan, determine a noise level for each of the employed processing sub-systems based on a corresponding noise model, and adaptively vary at least one of a gain and a dynamic range of an ultrasound image as a function of depth based on the noise levels.

Those skilled in the art will recognize still other aspects of the present application upon reading and understanding the attached description.

DETAILED DESCRIPTION

Figure 1:
FIG. 1 shows an example ultrasound image in which the front-end gain of the system amplifies the signal and the noise at larger depths to a degree that the noise manifests in a greyish background.
Figure 2:
FIG. 2 shows an example ultrasound image of FIG. 1 after the noise is reduced through the TGC curve.
Figure 3:
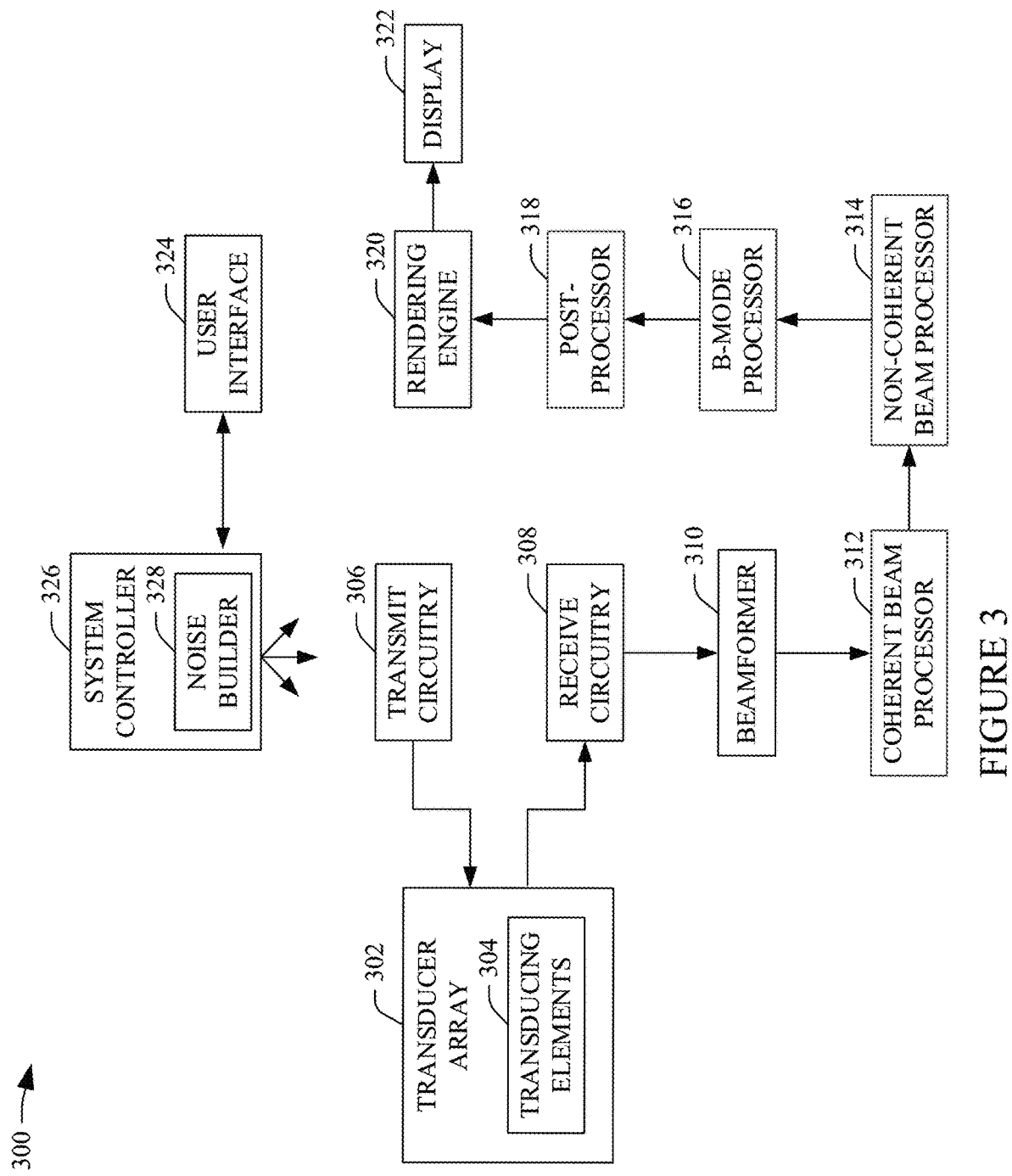
FIG. 3 schematically illustrates an example imaging system with a system controller augmented with a noise model builder.

FIG. 3 schematically illustrates an example ultrasound imaging system 300.

The ultrasound imaging system 300 includes a one- or two-dimensional transducer array 302 with one or more transducing elements 304. The transducing elements 304 are configured to emit a pressure wave in response to being excited by an electrical signal or pulse. Transmit circuitry 306 generates pulses that excite a set of transducing elements 304 to transmit a pressure wave. The transducing elements 304 are further configured to receive an echo pressure wave, which is generated in response to the emitted pressure wave interacting with structure (e.g. tissue, blood, etc.), and produce an analogic electrical (radio frequency, RF) signal indicative of the echo pressure wave.

Figure 4:
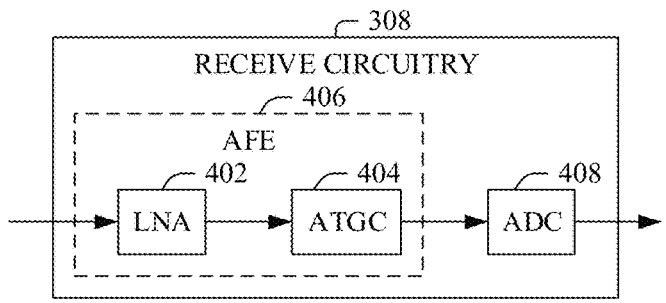
FIG. 4 schematically illustrates example receive circuitry of the imaging system that provides digital RF data.

Receive circuitry 308 receives and processes the electrical signal. FIG. 4 schematically illustrates an example of the receive circuitry 308. In the example of FIG. 4, the receive circuitry 308 includes a low-noise-amplifier (LNA) 402 configured to apply a fixed amplification. The receive circuitry 308 further includes an analog time gain compensation module (ATGC) 404 configured to apply a variable gain attenuation. The combination of at least the LNA 402 and the ATGC 404 is referred to herein as an analog front end (AFE) 406. The receive circuitry 308 further includes an analog-to-digital converter (ADC) 408 configured to convert the analogic electrical signal to a digital RF signal.

Figure 5:
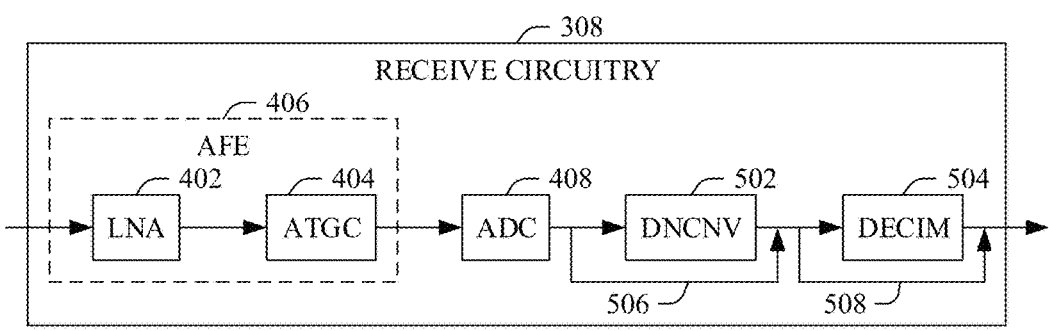
FIG. 5 schematically illustrates example receive circuitry of the imaging system that can be configured to provide either digital RF data, or digital complex IQ data at baseband.

FIG. 5 schematically illustrates a variation of the receive circuitry 308. This example is substantially similar to the example described in connection with FIG. 4 and further includes a down-converter (DNCNV) 502 configured to shift a center frequency of the signal to baseband (e.g., around zero Hertz, 0 Hz) and a decimator (DECIM) 504 configured to reduces the data rate. In one example, the shift of the center frequency of the RF signal to produce in-phase and quadrature-phase signal IQ is achieved by multiplying the RF signal by a complex sinusoid signal, e.g. I=RF×cos(wt), and Q=RF x−sin(wt). In one instance, the receive circuitry 308 is custom built or a purchased third-party component. The DNCNV 502 and/or the DECIM 504 can be bypassed, as shown by the bypass signal paths 506 and 508.

Figure 9:
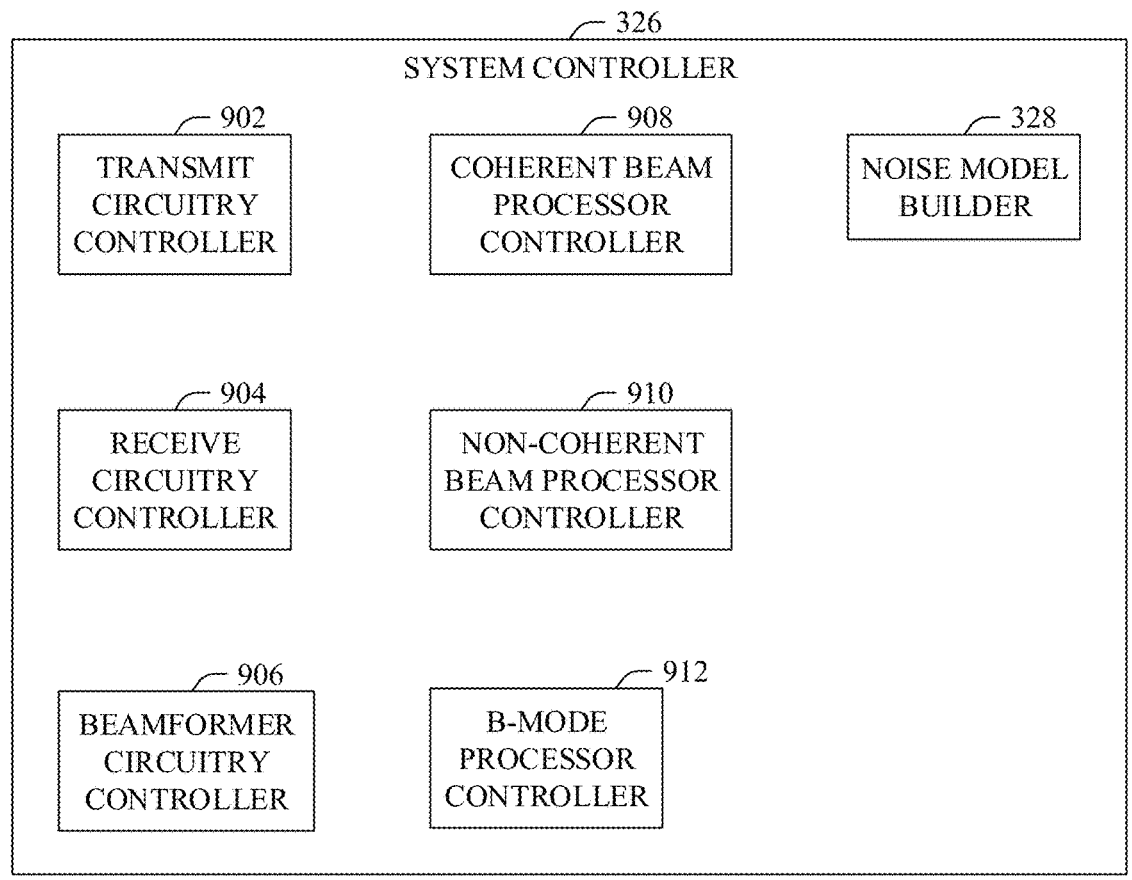
FIG. 9 schematically illustrates an example of the augmented system controller with a noise model builder and sub-controllers for each sub-system from FIG. 3.

Returning to FIG. 3, a beamformer 310 is configured to beamform the signal (or to pass data from a single channel of receive circuitry 308 directly to a noise model builder 328 of FIG. 9 for system calibration, which is described in greater detail below). For B-mode imaging, the beamforming may include delaying the signals from each of the elements 304 and summing the delayed signals when using the receive circuitry 308 of FIG. 4, and additionally producing baseband IQ data when using the receive circuitry 308 of FIG. 5. The delays used by the beamformer 310 account only for the propagation of the echo from the target back to the transducing elements 304 (or also include variations in propagation of the transmitted pressure wave in the case of synthetic transmit aperture focusing). The beamformer 310 produces a single beam or a plurality of beams using data from a single emit event.

Figure 6:
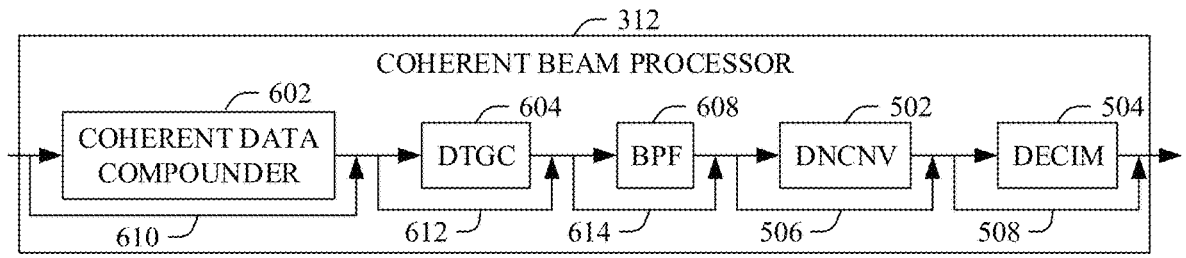
FIG. 6 schematically illustrates an example coherent beam processor of the imaging system.

A coherent beam processor 312 is configured to perform coherent beam processing. FIG. 6 schematically illustrates an example of the coherent beam processor 312. In FIG. 6, the coherent beam processor 312 includes a coherent data compounder 602 configured to perform coherent data compounding when some of the plurality of beams are spatially collocated (overlapping). A digital time compensation module (DTGC) 604 is configured to digitally amplify the signal with a gain factor, which is a function of depth. A band pass filter (BPF) 608 has a variable depth-dependent transfer function and limits the bandwidth of the echo plus noise data. The coherent beam processor 312 also includes the down-converter 502 and the decimator 504. Generally, the decimation and down-conversion can be performed anywhere in the data path prior to a non-coherent beam processor 314 (described next). The coherent beam processor 312 is configured so that some or all components can be bypassed, as shown by the bypass signal paths 610, 612, 614, 506 and 508.

Figure 7:
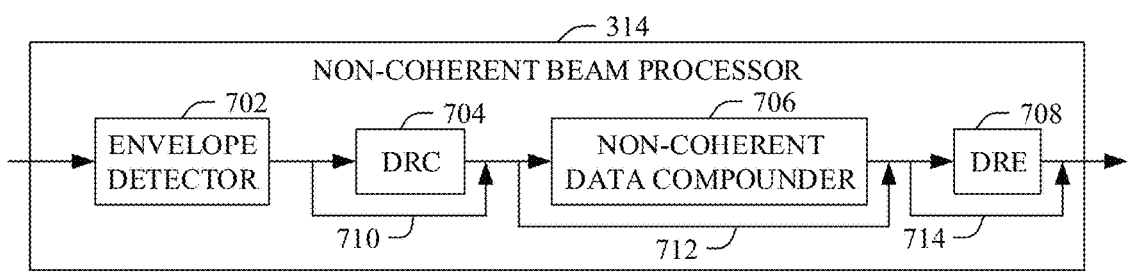
FIG. 7 schematically illustrates an example non-coherent beam processor of the imaging system.

Returning to FIG. 3, a non-coherent beam processor 314 is configured to perform non-coherent beam processing. FIG. 7 schematically illustrates an example of the non-coherent beam processor 314. In FIG. 7, the non-coherent beam processor 314 includes an envelope detector 702 configured to remove phase information from the beam data by, e.g.: $ENV=\sqrt{I^2+Q^2}$. A dynamic range compressor (DRC) 704 compresses the range of values of the envelope using a non-linear transformation function, such as logarithm, sigmoidal function, etc. A non-coherent data compounder 706 compounds envelope-detected data acquired using different sets of receive elements, different sets of transmit elements, echoes in response of transmit pulses with different center frequencies, or a combination thereof. A dynamic range expander (DRE) 708 applies an inverse function to the dynamic range compression function. The non-coherent beam processor 314 is configured so that some or all of processing blocks 704, 706 and 708 can be bypassed, as shown by the bypass signal paths 710, 712 and 714.

Figure 8:
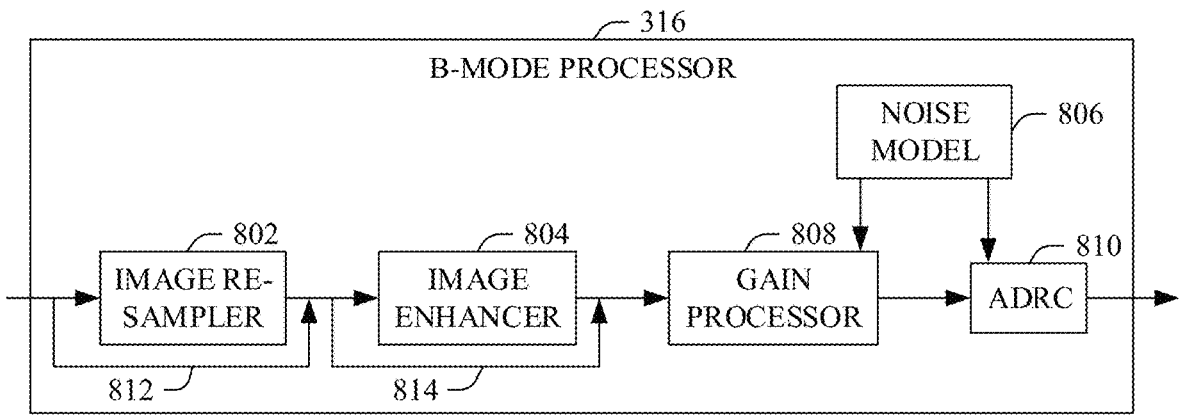
FIG. 8 schematically illustrates an example B-mode processor of the imaging system with adaptive gain and/or dynamic range compressor with a noise model.

Returning to FIG. 3, a B-mode processor 316 is configured to produce B-mode images. FIG. 8 schematically illustrates an example of the B-mode processor 316. In FIG.

8, an image re-sampler 802 scales the image so that it is suitable for subsequent processing. An image enhancer 804 applies image processing techniques to enhance edges and or other anatomical structures. A noise model 806 provides noise data calculated by the noise model builder 328 of FIG. 9 and controls the operation of a gain processor 808 and/or an adaptive dynamic range compressor 810 based on the estimated noise levels of the components employed for a scan (and not the bypassed components). The result of the gain processor 808 and the adaptive range compressor 810 is an electrical noise compensated signal/B-mode image. The B-mode processor 316 is configured so that some or all of processing blocks 802 and 804 can be bypassed, as shown by the bypass signal paths 812 and 814.

Returning to FIG. 3, a post-processor 318 is configured to process the electrical noise compensated signal. In one instance this includes converting the data back to its original format. A rendering engine 320 visually presents the noise reduced image via a display monitor 322. A user interface 324 includes one or more input devices (e.g. a button, a knob, a slider, a touch pad, etc.) and/or one or more output devices (e.g. a display screen, lights, a speaker, etc.). The user interface 324 can be used to select an imaging mode such as imaging with noise compensation with or without autogain as described herein, etc.

A system controller 326 is configured to control one or more of the components 306, 308, 310, 312, 314 and 316. FIG. 9 schematically illustrates an example of the system controller 326. In FIG. 9, the system controller 326 consists of controller sub-modules, each controlling the operation of a module the system 300. A transmit circuitry controller 902 controls the transmit circuitry 306. A receive circuitry controller 904 controls the operation of receive circuitry 308. A beamformer controller 906 controls the operation of beamformer 310. A coherent beam processor controller 908 controls the coherent beam processor 312. A non-coherent beam processor controller 916 controls non-coherent beam processor 314. A B-mode processor controller 910 controls B-mode processor 316. The system controller 330 further includes the noise model builder 328, which is configured to create a map of the noise levels along the signal path from the analog front end 406 of FIGS. 4 and/or 5 to the gain processor 808 and the adaptive dynamic range compressor 810 of FIG. 8.

Figure 10:
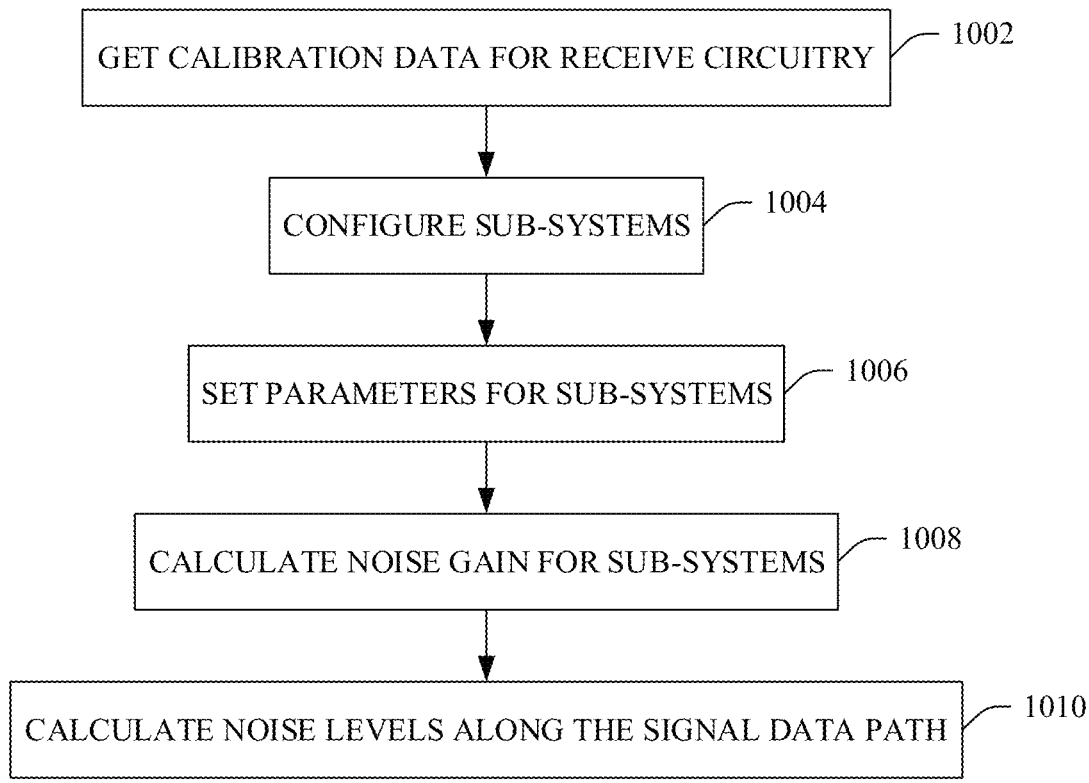
FIG. 10 illustrates an example of operation of the augmented system controller.

An example of an operation of the system controller 326 and the noise model builder 328 is illustrated in FIG. 10. At 1002, calibration data for the analog front end 406 is loaded. At 1004, the sub-systems of the system 300 are configured. The configuration includes the setup of the data path; namely, which blocks are bypassed and which are active/employed. At 1006, the parameters for the active/employed sub-systems are set. An example of such parameters is the coefficients of the band-pass filter 608. At 1008, the controllers for each sub-system calculate the direct current gain (DC gain) and alternating current gain (AC gain) for the sub-system they control. At 1010, the noise model builder 328 calculates the noise level along the signal data path.

This starts with the noise model builder 328 determining the noise level at the output of the receive circuitry 308. Then, the noise model builder 328 uses the model and the gain for the beamformer 310 to calculate the DC and AC noise levels at the output of the beamformer 310. The noise model builder 328 repeats this procedure for all of following blocks along the data path of the system 300. Intermediate values are cached for use by modules whose operation depends on signal-to-noise ratio. In one instance, this includes the B-mode processor, which uses the gain processor 808 and the adaptive dynamic range compressor 810. Other modes such as elasticity imaging, both free-hand strain imaging and shear-wave elastography also use signal-to-noise ratio as a quality control for the estimates.

Figure 11:
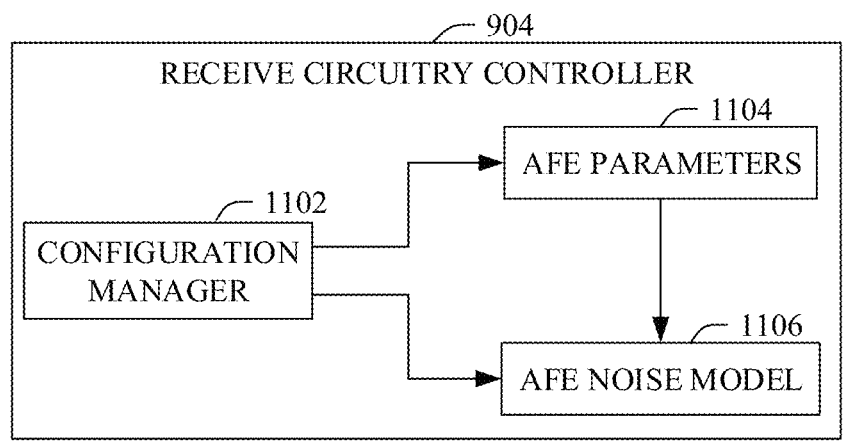
FIG. 11 schematically illustrates an example sub-controller for the receive circuitry.

To facilitate the system setup and the calculation of noise level, each sub-system of the system controller 330 contains at least three blocks—a configuration manager, a parameter block, and a noise model. By way of non-limiting example, FIG. 11 schematically illustrates one implementation of the receive circuitry controller 904 for the receive circuitry from FIG. 4. It contains a configuration manager 1102 that configures the mode of operation the receive circuitry 308, an analog front-end parameters calculator 1104 that sets the sampling frequency, the gain of the low-noise amplifier (LNA) 402 and the attenuation/gain voltage of the analog time gain compensation block 404, and an analog front-end noise model 1106. The specific parameters and ranges depend on the hardware architecture of a scanner.

Figure 12:
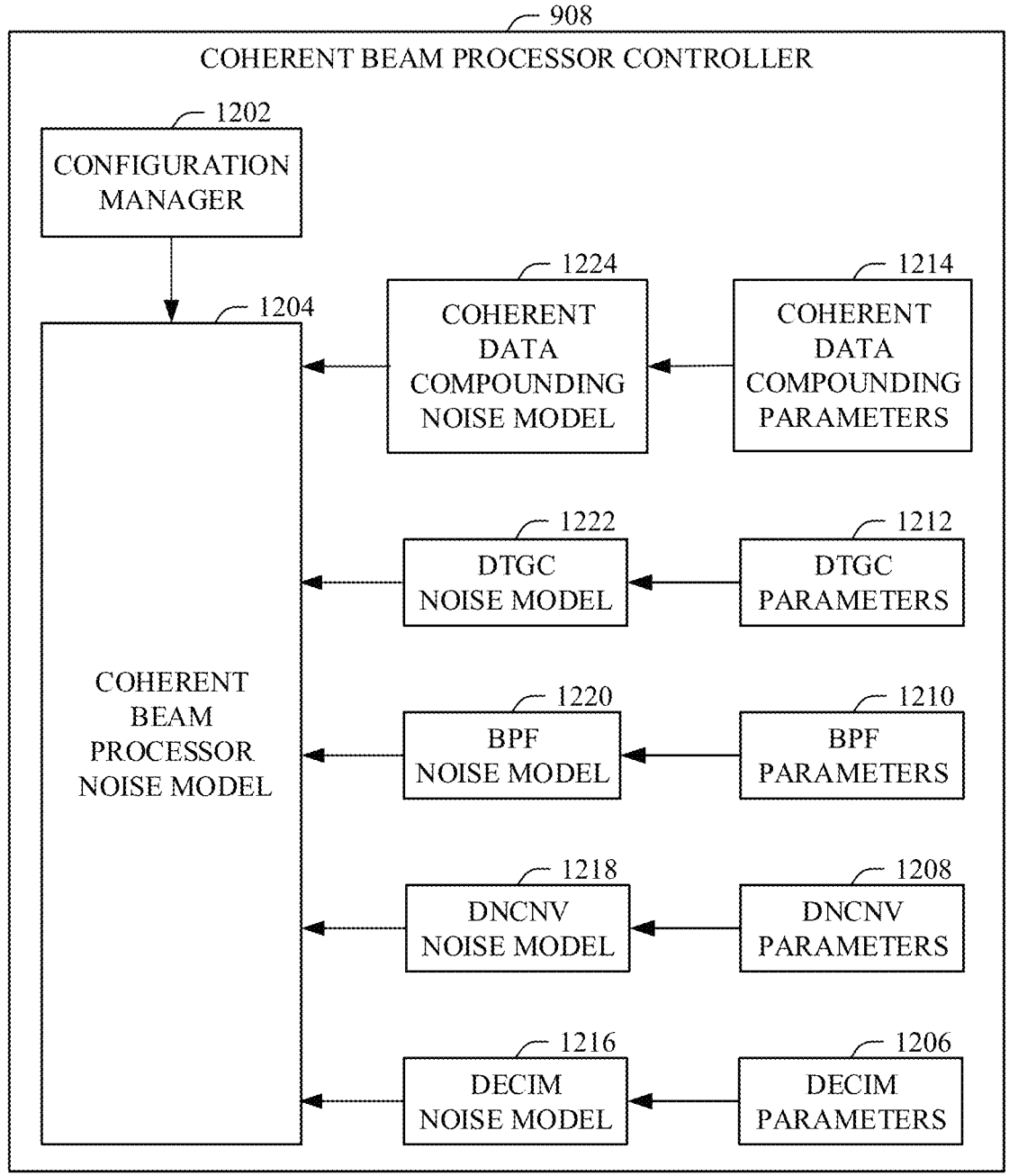
FIG. 12 schematically illustrates an example controller for the coherent beam processor.

FIG. 12 schematically illustrates another example of a sub-system controller, where the sub-system further consists of blocks that can be individually configured and enabled or disabled. The example in FIG. 12 is of the coherent beam processor controller 908, which controls the operation of the coherent beam processor 312. A configuration manager 1202 configures the path of the signal through the coherent beam processor 312 based on a coherent beam processor noise model 1204. There is a separate parameter block in the controller 908 responsible to set the parameters for a respective processing block in the processor 312.

Decimation parameters block (DECIM) 1206 sets up decimation block 504. Down conversion parameters block (DNCNV) 1208 sets up down-conversion block 502. Band pass filter parameters block (BPF) 1210 sets up band pass filter 608. Digital time gain compensation parameters (DTGC) 1212 sets up digital time gain compensation block 604. Coherent data compounding parameters block 1214 sets up the operation of coherent data compounding block 602. Each parameter block is paired with a respective noise model block 1216, 1218, 1220, 1222 and 1224 that can estimate the noise at the output of the corresponding processing block operating with a given set of parameters. The block 1224 models the noise in block 602, 1222 models the noise of 604, 1220 models the noise of 608, 1218 models 502, and 1216 models 504.

Figure 13:
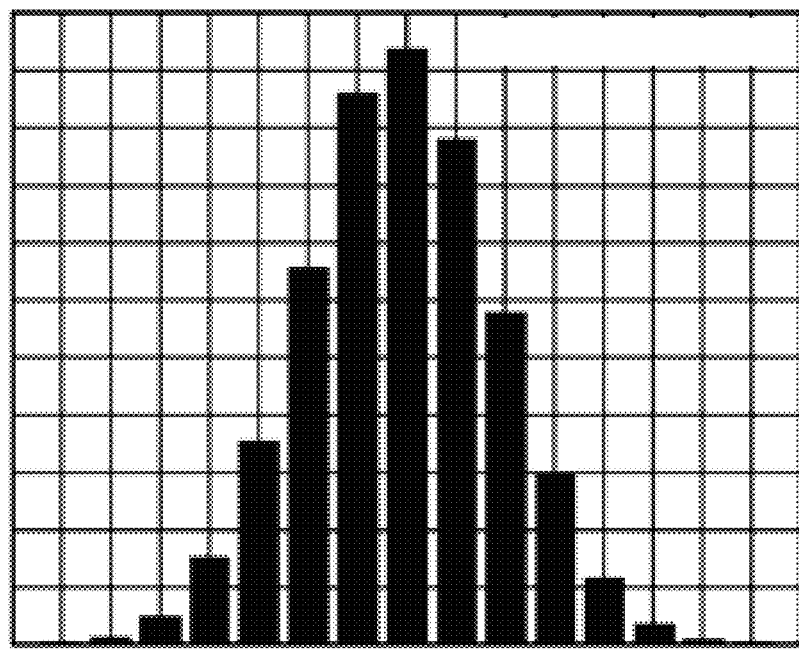
FIG. 13 illustrates a distribution of values of electrical noise for a given gain setting for the receive circuitry.
Figure 14:
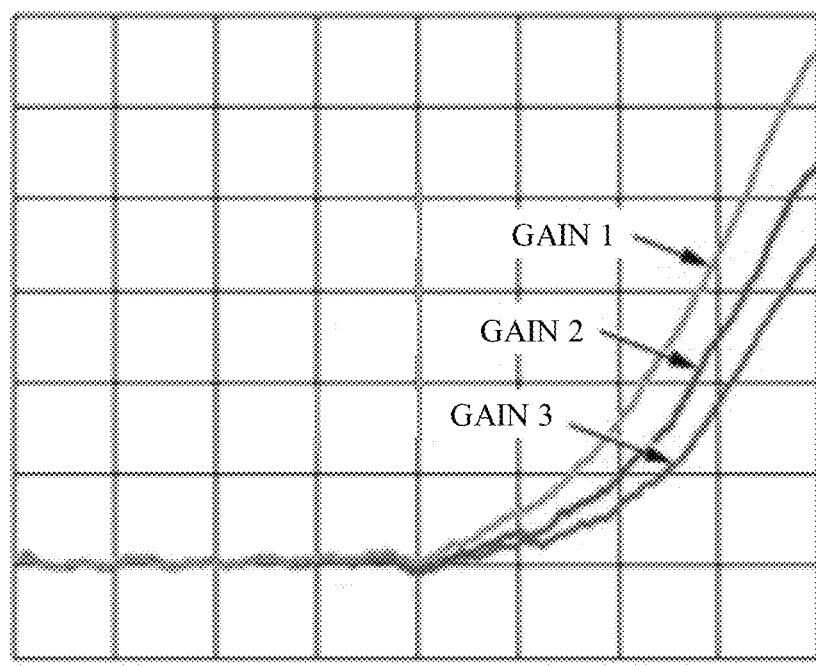
FIG. 14 illustrates the noise level of the receive circuitry.

The noise models fall into several (but not limited to) categories: noise model of analog components; noise model of linear digital processing blocks; noise model of non-linear digital processing blocks with constant behavior; noise models of non-linear digital processing blocks that represent non-trivial function. Noise models of analog components need calibration. FIG. 13 illustrates a histogram of the sample values of the receive circuitry 308 from FIG. 4 in the absence of input signal. FIG. 14 shows the noise level of the receive circuitry 308 from FIG. 4 for different settings of the gain of the low-noise amplifier (LNA) 402. The conditions at which every receive circuitry 308 operates depends on input impedance, local sources of noise, electro-magnetic isolation etc. There are variations from device to device of the same model. The noise model 1106 for the receive circuitry (AFE 406) 308 needs calibration data.

Figure 15:
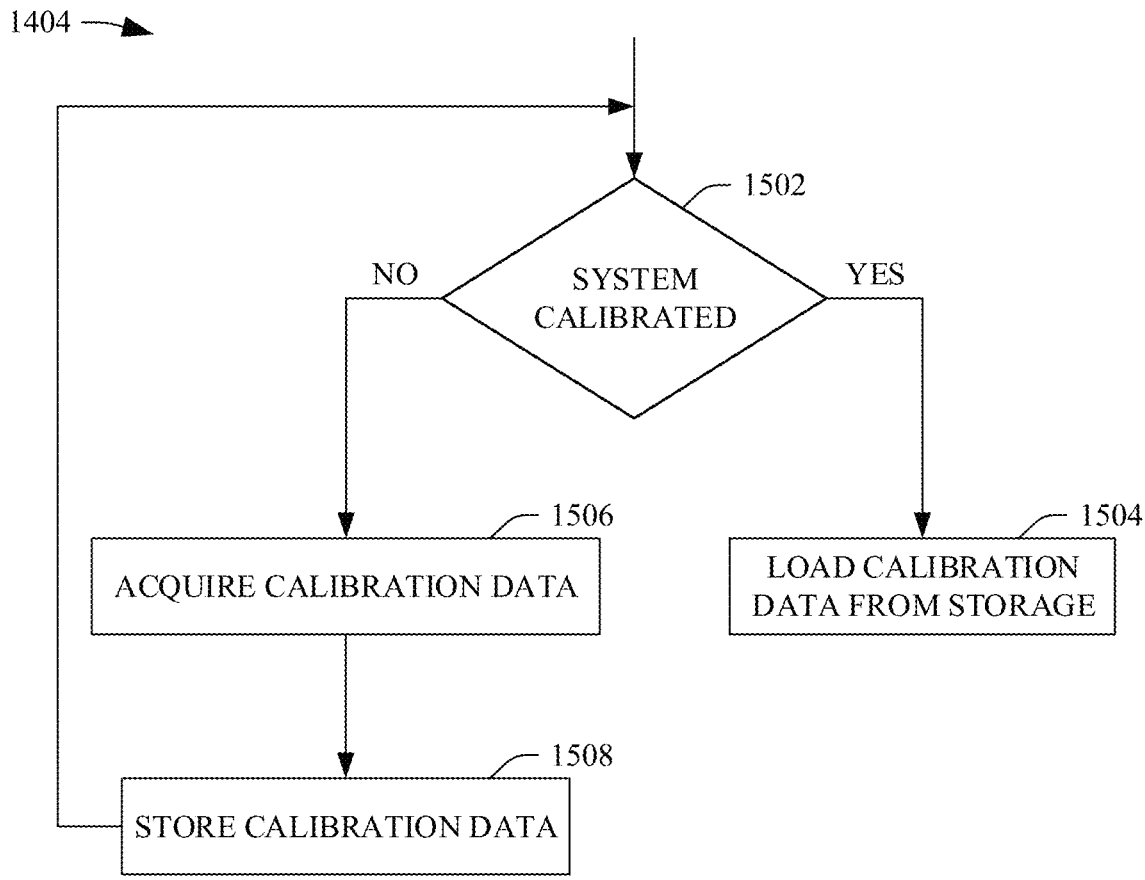
FIG. 15 illustrates an example of operation of the acquisition of calibration data and loading of data for use by the noise model.
Figure 16:
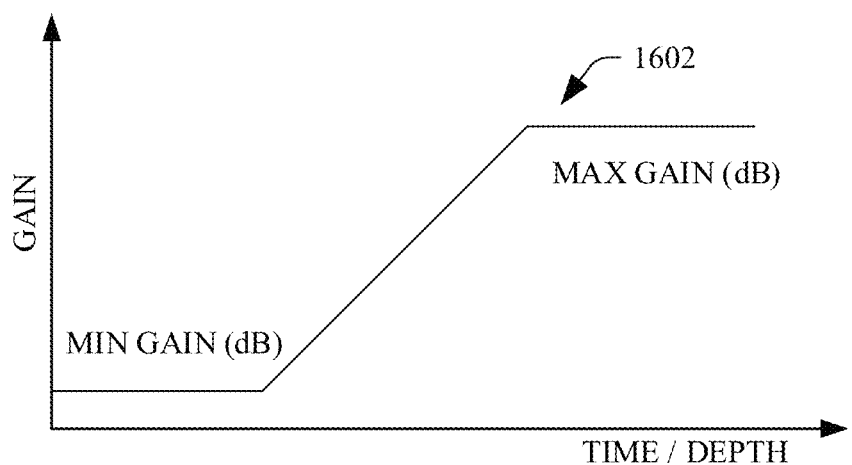
FIG. 16 illustrates a gain variation for a given setup used during the acquisition of calibration data.

The step 1002 of the operation of the system controller (FIG. 10) can be described with the chart shown in FIG. 15. At 1502, it is determined if the system is already calibrated. If the system is already calibrated, then at 1504 the calibration data is loaded from memory storage. If the system not calibrated (e.g., used for first time or first time after an update) then at 1506 calibration data is acquired. At 1508, the acquired calibration data is stored in the memory storage for subsequent use. To acquire calibration data, the beamformer is 310 is configured to pass-through data from a single receive channel only. All delays values are set to 0. The transmit circuitry 306 is configured not to send any electric signal. All processing blocks in system 300 are configured such as raw channel data is recorded by system controller 326. Channel data are recorded for all supported configuration of the receive circuitry 308 such as LNA gain, sampling rate, etc. For each configuration control voltage for the analog time gain compensation block 404 is varied as shown in FIG. 16. A TGC curve 1602 starts at minimum gain where it is kept for the first third of the acquisition, then it increases to maximum gain where it stays for the last third of the acquisition. The slope of the increase is chosen such as to avoid transient effects in the ATGC block 404.

The noise for the analog front end 406 can be modeled with a linear function:

$$v_N = v_{ATGC} + TGC \cdot v_{LNA},$$

where $v_N$ is the root-mean-square (RMS) noise level at the output of the AFE 406, $v_{ATGC}$ is the RMS voltage of the thermal noise of the ATGC 404 and $v_{LNA}$ is the RMS voltage of the thermal noise at the output of the LNA 402. TGC is the value of the time gain compensation curve 1602. Using the first third of the TGC curve 1602 from the calibration measurement allows calculating the RMS value $v_N$ at minimum TGC. The last part of the data acquired at maximum gain (gain illustrated in FIG. 16) gives an estimate of the RMS value $v_N$ at maximum TGC. These two values for $v_N$ enable the calculation of the model constants $v_{ATGC}$ and $v_{LNA}$. These two constants are calculated for all configurations of the AFE 406 and stored in the scanner at 1504. The AFE 406 produces white Gaussian zero-mean noise as shown in FIG. 13. The RMS value $v_N$ is equal to the standard deviation of the noise values $\sigma_N = v_N$. The mean value of the noise of the AFE 406 is $\mu_N = 0$. Other models are contemplated herein. Generally, the model employed will depend on the configuration of the AFE, which can be different than the AFE 406 described herein.

For linear filters in the system, including beamforming and coherent- and non-coherent beam compounding the gain of the AC part of the noise is:

$$G_{AC} = \sqrt{\sum_{i=0}^{N-1} h_i^2},$$

where $h_i$ are the filter coefficients and N is the number of filter coefficients. The DC gain of the filter is:

$$G_{DC} = \sum_{i=0}^{N-1} h_i.$$

If $\sigma_i$ is the standard deviation of the noise at input of a linear filter, and $\mu_i$ is the mean value the noise at the input of a linear filter, then the standard deviation and mean value of the noise at the output of the filter $\sigma_o$ and $\mu_o$, respectively are:

$$\mu_o = G_{AC} \cdot \sigma_i, \text{ and}$$

$$\mu_o = G_{DC} \cdot \mu_i.$$

The RMS value $v_o$ of the noise at any step can be found as $$v_o = \sqrt{\sigma_o^2 + \mu_o^2}.$$

The noise level of the output of non-linear processing blocks such as envelope detector 702 and the dynamic range compressor 704 can be done using the probability density function of the noise values at the input and the conversion function:

$$E\{y^q\} = \frac{\int_a^b (F(x))^q w(x) dx}{\int_a^b w(x) dx},$$

where $E\{y^q\}$ is the expectation of the q:th moment of the output value y, F(x) is the transfer function (y=F(x)) and w(x) is the probability density function of the noise x at the input of the non-linear processing block. The limits a and b are typically chosen such as to contain 99% of the energy of the noise signal. The mean of the output noise is found as $\mu_y = E\{y^1\}$, and the standard deviation of the output noise is found as $\sigma_y = \sqrt{E\{y^2\} - (E\{y^1\})^2}$. The integration can be analytical or numerical depending on the algorithm implemented in a specific processing block.

If there are different parameters, then the calibration procedure should fit the model. The following describes another suitable calibration. For this calibration, a series of measurements with a fixed gain (TGC) is used instead of the curve show in FIG. 16. The curve in FIG. 16 is well-suited for using two support levels (at min and max) and a curve minimizes calibration time. With another calibration, a beam-sum is passed through the beamformer instead of single-channel data through the beamformer, and then gets the average noise level from the AFE by dividing the noise of the beam-sum by the gain of the beam sum (a gain of the beamformer 310, and possibly followed by the coherent beam processor 312).

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array configured to produce and output an analog electrical signal indicative of a received echo wave during data acquisition and in absence of the received echo wave during system calibration;
   receive circuitry, including:
      an analog front end, comprising:
         a low-noise amplifier configured to apply a fixed amplification to the analog electrical signal; and
         an analog time gain compensation module configured to apply a variable gain attenuation to the amplified analog electrical signal,
      wherein the receive circuitry outputs a signal that during the data acquisition is indicative of the received echo wave and electrical noise of the analog front end and that during the system calibration is indicative of the electrical noise of the analog front end;

processing sub-systems configured to process the signal indicative of the received echo wave and the electrical noise of the analog front end to generate an image; and a system controller configured to:
determine a noise level of the electrical noise of the analog front end during the system calibration by:
determining a first noise level of the analog front end for a fixed amplification level and a first pre-determined variable gain attenuation level for a first increasing depth range; increasing the first pre-determined variable gain attenuation level to a second pre-determined variable gain attenuation level over a second increasing depth range, wherein the second increasing depth range is greater than the first increasing depth range;
determining a second noise level of the analog front end at the second pre-determined variable gain attenuation level for a third increasing depth range, wherein the third increasing depth range is greater than the second increasing depth range; and
determining the noise level of the electrical noise of the analog front end based on the first noise level, the second noise level and a noise model for the analog front end;
configure the processing sub-systems, wherein each of processing sub-systems includes multiple processing blocks, and the configuring determines which of the processing blocks are employed and which of the processing blocks are bypassed for a scan; and
determine a processing sub-system noise level for each of the processing sub-systems based on the corresponding employed processing blocks and a corresponding noise model,
wherein the processing sub-systems includes a processor configured to adaptively vary at least one of a gain and a dynamic range of the image as a function of depth based on the noise level of the electrical noise of the analog front end and the noise level for each of the employed processing sub-systems.

2. The ultrasound imaging system of claim 1, wherein the noise level of the electrical noise of the analog front end includes a thermal noise at an output of the low-noise amplifier and a thermal noise of the analog time gain compensation module.

3. The ultrasound imaging system of claim 1, wherein the system controller performs the system calibration upon first use of the ultrasound imaging system.

4. The ultrasound imaging system of claim 1, wherein the system controller is configured to determine the noise level of the electrical noise of the analog front end based at least on a root-mean-square voltage of a thermal noise of the analog time gain compensation module and a root-mean-square voltage of a thermal noise at an output of the low-noise amplifier.

5. The ultrasound imaging system of claim 1, wherein the noise level of the electrical noise of the analog front end includes:

$$v_N = v_{ATGC} + TGC \cdot v_{LNA},$$

where $v_N$ is a root-mean-square voltage of the noise level of the electrical noise at an output of the analog front end, $v_{ATGC}$ is a root-mean-square voltage of a thermal noise of the analog time gain compensation module, $v_{LNA}$ is a root-mean-square voltage of a thermal noise at an output of the low-noise amplifier, and TGC is a value of the variable gain attenuation level at a given depth.

6. The ultrasound imaging system of claim 1, wherein the system controller is configured to record the noise level of the electrical noise of the analog front end in memory.

7. The ultrasound imaging system of claim 6, wherein the system controller is configured to load the recorded noise level of the electrical noise of the analog front end prior to the data acquisition.

8. The ultrasound imaging system of claim 1, wherein the transducer array includes a plurality of transducing elements, and the system controller determine a noise level for each channel of the receive circuitry for each of the plurality of transducing elements.

9. The ultrasound imaging system of claim 8, wherein the system controller determines a plurality of noise levels for a channel of the receive circuitry, including a noise level for each low-noise amplifier gain level for a plurality of low-noise amplifier gain levels for the low-noise amplifier.

10. The ultrasound imaging system of claim 9, wherein the receive circuitry further includes an analog-to-digital converter configured to convert the amplified analog electrical signal to a digital signal, and the system controller further determines the plurality of noise levels for each channel of the receive circuitry for each sampling frequency of the analog-to-digital converter for a plurality of sampling frequencies for the analog-to-digital converter.

11. The ultrasound imaging system of claim 1, wherein the system controller performs the system calibration upon first use of the ultrasound imaging system after a system update.

12. The ultrasound imaging system of claim 1, wherein the first pre-determined variable gain attenuation level is a minimum gain level.

13. The ultrasound imaging system of claim 12, wherein the second pre-determined variable gain attenuation level is a maximum gain level.

14. The ultrasound imaging system of claim 13, wherein the variable gain attenuation is linearly increased from the first pre-determined variable gain attenuation level to the second pre-determined variable gain attenuation level.

15. The ultrasound imaging system of claim 1, wherein the receive circuitry further includes:
a configuration manager that configures a mode of operation the receive circuitry;
analog front end parameters that set a sampling frequency, a gain of the low-noise amplifier, and an attenuation/gain voltage of the analog time gain compensation module; and
the noise model for the analog front end.

16. The ultrasound imaging system of claim 15, wherein an input of the noise model for the analog front end receives the analog front end parameters.

17. The ultrasound imaging system of claim 1, wherein each of the processing sub-systems includes:
a configuration manager that configures a corresponding mode of operation the corresponding processing sub-system;
corresponding parameters for the corresponding processing sub-system; and
a corresponding noise model for the corresponding processing sub-system.

18. The ultrasound imaging system of claim 1, wherein a slope of the variable gain attenuation avoids transient effects in the analog time gain compensation module.

* * * * *